United States Patent [19]

Powell et al.

[11] Patent Number: 5,459,056
[45] Date of Patent: Oct. 17, 1995

[54] HUMAN T CELL LINE CHRONICALLY INFECTED WITH HIV

[75] Inventors: Douglas M. Powell, Silver Spring, Md.; Kathleen A. Clouse, Arlington, Va.; Thomas M. Folks, Lithonia, Ga.

[73] Assignee: The United States of America as represented by the Department of Health and Human Services, Washington, D.C.

[21] Appl. No.: 919,378

[22] Filed: Jul. 29, 1992

Related U.S. Application Data

[63] Continuation of Ser. No. 394,079, Aug. 28, 1989, abandoned.

[51] Int. Cl.$^6$ .................... C12N 5/00; C12N 7/00
[52] U.S. Cl. .................... 435/240.2; 435/240.25; 435/237; 435/239; 435/235.1; 435/5

[58] Field of Search .............. 435/5, 235.1, 239, 435/240.2, 240.25

[56] References Cited

U.S. PATENT DOCUMENTS 4,968,601  11/1990  Jacobson et al. .................... 435/5

OTHER PUBLICATIONS

Folks et al. (1986) Science, vol. 231, pp. 600–602.
Clouse et al. (1989, Jan. 15) The Journal of Immunology, vol. 142, pp. 431–438.

Primary Examiner—Garnette D. Draper
Assistant Examiner—Gian P. Wang
Attorney, Agent, or Firm—Needle & Rosenberg

[57] ABSTRACT

A human T cell clone containing an integrated copy of HIV in a latent state, but inducible to productive replication by an activating agent is provided. The clone of the present invention allows in vitro screening of anti-HIV drugs.

1 Claim, 7 Drawing Sheets

HUMAN T CELL LINE CHRONICALLY INFECTED WITH HIV

This is a continuation of application Ser. No. 07/399,079, filed on Aug. 28, 1989, which was abandoned upon filing hereof.

The present invention is related to providing a chronically or latently infected human T cell clone containing an integrated copy of human immunodeficiency virus (HIV) in a latent state of replication and inducible to productive state by activating agents.

The interval of time between initial Infection with HIV-1, the etiologic agent of AIDS, and clinical evidence of severe immunosuppression and disease can span several years (Melbye et al, 1986, *Ann. Intern. Med.*, 104:496; Fauci, A. S., 1988, *Science*, 239:617), suggesting that latent or chronic, low level infections predominate in most infected individuals. The mechanisms involved in the in vivo progression from a latent or chronic HIV infection to a productive infection have not been clearly determined. It is possible that activation signals are necessary, because the level of virus replication directly correlates with the state of T cell activation in vitro (McDougal et al, 1985, *Immunol*, 135:3151; Folks et al, 1986, *J. Immunol.* 136:4049) and a broad range of activation signals can induce the expression of HIV in infected cell lines. In vitro studies have shown that non-productive infections of normal T lymphocytes or T cell lines with HIV-1 can be converted to productive infections by subjecting the cells to different activation signals including mitogens (McDougal et al, supra, Folks et al, supra; Zagury et al, 1986, *Science*, 231:850), Ag (Margollck et al, 1987, *J. Immunol.*, 138:1719), and phorbol esters (Harada et al, 1986, *Virology*, 154:249). Recent studies have also demonstrated that chronically HIV-infected human promonocyte clones could have virus production augmented either by using phorbol esters (Folks et al, 1988, *J. Immunol.*, 140:117) or human cytokines (Folks et al, 1987, *Science*, 238:800). Furthermore, simultaneous co-transfection of HIV-susceptible cells with a plasmid containing the HIV-1 long terminal repeat and a plasmid containing the tat-III gene and/or heterologous vital DNA has resulted in activation of the HIV-long terminal repeat (Gendelman et al, 1986, *Proc. Natl. Acad. Sci. USA*, 83:9759; Mosca et al, 1987, *Nature*, 325:67; Davis et al, 1987, *Proc. Natl. Acad. Sci. USA*, 84:8642)

Inasmuch as $CD4^+$ T lymphocytes are primarily the cells killed by HIV and this cell population is the most relevant with regard to immunosuppression, it was deemed most desirable to determine whether non-productively infected human T cells could be converted to a productive infection by exposure to cellular derived substances, such as cytokines. Such a cell line was not heretofore known or described.

SUMMARY OF THE INVENTION

It is, therefore, an object of the present invention to provide a stable cell line wherein HIV infection remains latent or non-productive, but could be converted to proliferative state by suitable activating agents.

It is a further object of the present invention to provide an in vitro system for assessing antiviral activity of a putative anti-HIV agent.

It is an additional object of the present invention to provide a positive control for the PCR technique by quantitating the amount of vital DNA present in a sample.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2B shows immunofluorescent analysis of HIV-1 protein expression as described for FIG. 2A, but cultured with LPS-M0 SN.

FIG. 2C shows immunofluorescent analysis for HIV-1 protein expression as described for FIG. 2A, but cultured with PMA.

FIG. 3B shows kinetics of induction of ACH-2 cells and dose response to LPS-M0 SN similar to that described for FIG. 3A. Two time points determined by kinetics as optimal for induction (48 and 72 h) were selected to establish the response to varying concentrations of LPS-M0 SN as determined by RT activity.

FIG. 6B shows monokine profiles of those supernatants tested for biological activity as described for FIG. 6A. Levels of human TNF-α were determined by ELISA using rabbit polyclonal antibody to rTNF-α (Cetus Corp.) ( --- ). Human IL-1β levels were determined by an RIA method (Cistron Corp.) ( --- ). Data for both monokines are expressed in pg/ml.

DETAILED DESCRIPTION OF THE INVENTION

Figure 1:
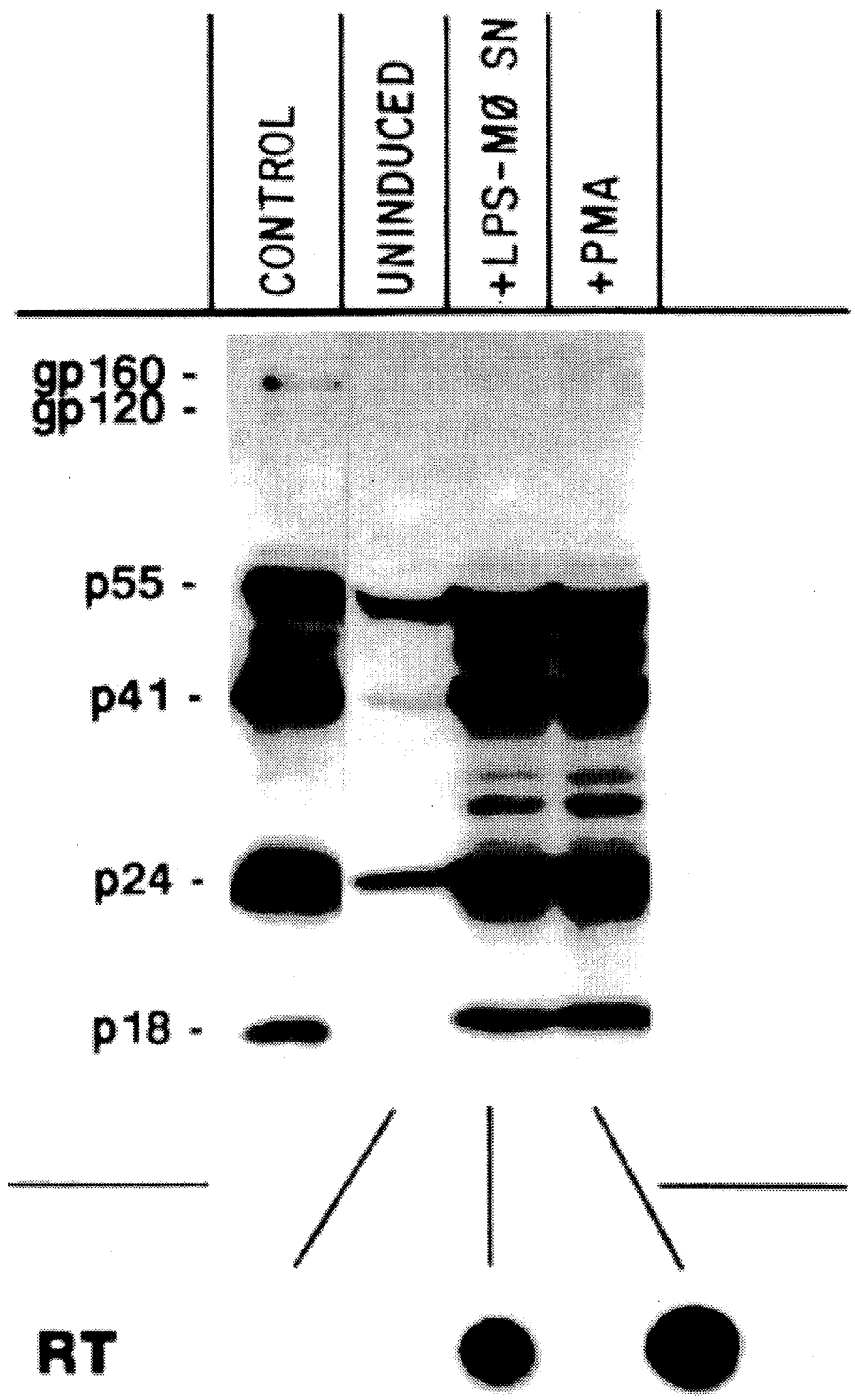
FIG. 1 shows immunoblot and reverse transcriptase analyses of HIV-1 protein expression in ACH-2 cells before and after induction. ACH-2 cells ($5 \times 10^6$) were cultured in complete medium alone or in complete medium containing either PMA ($10^-M$) or LPS-M0 SN (10%) for 48 h. Total cell lysates were prepared from pelleted cells and a control lysate was prepared from HIV-1 infected A3.01 cells. Immunoblots were generated as described in *Materials and Methods* and the major vital proteins reacting with the AIDS patient serum are identified. Culture supernatants collected from the ACH-2 cells were also assayed for RT activity using [$^{32}P$] dTTP.

The above and various other objects and advantages of the present invention are achieved by a human T cell clone containing an integrated copy of human immunodeficiency virus in a latent state, but said virus being inducible to multiplicative replication by a suitable activating agent.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The examples are illustrative only and not limiting.

MATERIALS AND METHODS

Culture medium.

The tissue culture medium (complete medium) used was RPMI 1640 medium (M. A. Bioproducts, Rockville, Md.) supplemented with 10 mM HEPES buffer, 2 mM $_L$-glutamine, 100 U/ml of penicillin, 100 μg/ml of streptomycin, and 10% v/v of heat-inactivated FCS (Biofluids, Inc., Rockville, Md.), unless otherwise indicated. Primary HIV-1 infection and cell cloning. The lymphadenopathy-associated virus strain of HIV-1 was used in all studies. A total of $1\times10^4$ A3.01 cells (Folks et al, 1985, *Proc. Natl. Acad. Sci. USA*, 82:4539) was infected in 1 ml of stock HIV-1 at a multiplicity of infection equal to one infectious unit per cell. After adsorption for 4 h at 37° C., the cell suspension was diluted in 5 ml of complete medium and incubated an additional 24 h. The cells were then washed and maintained at 37° C. in 5 ml of complete medium in a 25-cm$^2$ tissue culture flask (Corning, Corning, N.Y.) for 4 days before cloning. The infected cells were then cloned in 10 round-bottom plates (Costar, Cambridge, Mass.) at 0.2 cells/well in a final volume of 0.2 ml of complete medium. Of the 192 clones subsequently derived, a single clone (ACH-2) was selected for this study based on its ability to produce syncytia after co-cultivation with CD4$^+$, uninfected A3.01 cells and to produce detectable levels of RT$^4$ activity in cell supernatants collected after induction with either IUdR or PMA. ACH-2 cells were expanded and cryopreserved for subsequent experimentation.

RT assays.

The reverse transcriptase (RT) assay used for some experiments was carried out as described by Strebel et al (1987, *Nature*, 328:728) and Willey et al (1988, *J. Virol.*, 62:139). Briefly, 10 μl of supernatant containing RT were added to a cocktail containing poly (A), oligo(dT) (Pharmacia, Inc., Piscataway, N.J.), MgCl$_2$, and [$^{32}$P]dTTP (Amersham Corp., Arlington Heights, Ill.) and was incubated for 2 h at 37° C. Then 10 μl of the cocktail was spotted onto DE81 paper, dried, and washed in 1×saline-sodium citrate buffer. The paper was dried and exposed to x-ray film for 8 h at −80° C. RT assays for all remaining experiments were done using [$^3$]-dTTP as the radiolabel and were performed as follows. Briefly, 50 μl of supernatant containing RT were diluted with an equal volume of Tris buffer, pH 7.8, containing Triton X-100, then 25 μl was added to a cocktail containing poly(A), oligo(dT), MgCl$_2$, and [$^3$H]-dTTP and incubated for 1 h at 37° C. A total of 50 μl of the reaction mixture was spotted onto nitrocellulose paper, dried, and washed in TCA containing sodium pyrophosphate, them 5% TCA alone, followed by 50% ethanol. The filters were dried and counted on a Beckman scintillation counter (LS 8801) (Beckman Instruments, Inc., Palo Alto, Calif.). Values shown reflect the average of duplicate samples (counts/min/8 μl) which differ by not more than 15%.

Cell surface characterization by Flow Cytometry (FCM).

Aliquots of cells ($1\times10^6$) were prepared for FCM by washing twice in PBS containing BSA and 0.05% sodium azide (FCM buffer), and resuspended in 50 to 100 μl of FCM buffer. Directly fluoresceinated mAb (2 μl) was added to cells and incubated for 30 min on ice at 4° C. Cells were then washed with FCM buffer, incubated in 1 ml of 1% paraformaldehyde for 10 min, washed, and resuspended in FCM buffer at $1\times10^6$ cells/ml. mAb used were Leu 1 (CD5), Leu 3 (CD4), Leu 4 (CD3), Leu 2 (CDS), and Leu M3, as well as antibodies against HLA-DR, MHC class I Ag. and transferrin receptors (Becton Dickinson, Sunnyvale, Calif.). FCM analysis was carried out using a FACS analyzer (Becton Dickinson). Cells to be analyzed were identified using a vol versus 90° side scatter gate and intensity of fluorescence was recorded using a three decade log scale and displayed on a linear scale.

Detection of HIV-encoded proteins by immunoblotting.

Total cell lysates were prepared from HIV-infected A3.01 cells or from uninduced or induced ACH-2 cells ($5\times10^6$) using Chaps buffer and 2% deoxycholate in Chaps buffer. Proteins from the solubilized cells were separated on 10 to 20% gradient SDS-polyacrylamide gels (Integrated Separation Systems, Newton, Mass.), by the method of Laemmli (1970, *Nature*, 227:680) and transferred to nitrocellulose membranes (Towbin et al, 1979, *Proc. Natl. Acad. Sci. USA*, 76:4350). The filters were then treated with 5% non-fat dry milk in 10 mM Tris, pH7.4, and 155 mM NaCl (TN) for 30 min, and further rinsed in TN buffer containing 0.3% Tween-20, 0.5% Nonidet P-40 (TN-TN), and 1% BSA. Serum from an individual AIDS patient was diluted in TN-TN (1/1000) containing 3% BSA and was incubated for 3 h at room temperature (approximately 22°–24° C.) with the nitrocellulose filters. The membranes were then washed three times in TN-TN buffer, incubated for 2 h with [$^{125}$I]-protein A (200,000 dpm/ml), washed, air dried, and exposed to x-ray film at −80° C.

Detection of HIV-encoded proteins by indirect immunofluorescence.

Cells were cytocentrifuged, air dried, and fixed in 50% acetone/50% methanol for 10 min at −20° C. Serum from a single AIDS patient was diluted in PBS (1/1000), added to the slides for 30 min, and then removed by washing three times in PBS. FITC-conjugated goat anti-human Ig antibody (1/500; Jackson Immunoresearch Laboratories, Avondale, Pa.) was added to the slides for 30 min, followed by three additional washes in PBS. Coverslips were added with a glycerol layer and the slides were observed for fluorescence-positive cells on a Nikon Labfot fluorescence microscope.

Isolation of human PBMC.

Mononuclear cells were isolated from the leukopheresed blood of normal individuals after Ficoll-Hypaque gradient centrifugation (Boyum, A., 1968, *Scand. J. Clin. Lab. Invest.*, 21:77).

The interface cells were washed three times with PBS then resuspended in supplemented RPMI medium containing no serum.

Isolation of human T lymphocytes.

Human T lymphocytes were isolated by negative selection using a cocktail of mAb (T Lympho-kwik Reagent: produced at University of California, Los Angeles and distributed by One Lambda, Inc., Los Angeles, Calif.). As reported elsewhere (Clouse, et al, 1987, *J. Immunol. Methods*, 105:253), isolated PBMC ($20\times10^6$) suspended in RPMI medium without serum were pelleted by centrifugation (10 min at 1500 rpm), then resuspended in 700 µl of T Lympho-kwik. The cell suspension was incubated 60 min in a sterile, capped microcentrifuge tube in a 37° C. water bath, mixing every 15 min. The cells were overlayed with 200 µl of unsupplemented RPMI medium, centrifuged at 200×g for 2 min, after which supernatant and dead cell debris were removed. The cell pellet was resuspended and washed two times in RPMI, followed by centrifugation at 1000×g for 1 min, and suspension in serum-free RPMI.

Isolation of MO by Countercurrent Centrifugal Elutriation (CCE).

Human MO were fractionated from isolated [PBMC by employing a Beckman CCE system (Stevenson et al, 1981, In: *Manual of Macrophage Methodology*, H. B. Herscowltz, H. T. Holden, J. A. Bellanti, and A. Gaffes, eds. Marcel Decker Press, New York) consisting of a J-21 centrifuge and a JE-6 elutriator rotor. For this procedure, isolated PBMC ($1\times10^9$) that had been washed twice in PBS and once in elutriation buffer were suspended in 50 ml of elutriation buffer before separation. The elutriation buffer was a sodium phosphate buffer, pH 7.2, containing 5% dextrose, 1.25% human serum albumin (Armour Pharmaceutical Co., Kankakee, Ill.), 50 µg/ml gentamicin sulphate, 10 U/ml of penicillin, 10 µg/ml of streptomycin, and 250 ng/ml of Amphotericin B. Before use, the CCE system was sterilized with 500 ml of 70% ethanol, rinsed with 500 ml of sterile distilled water, then brought into isotonic range with 500 ml of sterile PBS followed by 200 ml of elutriation buffer. The PBMC were pumped directly into the elutriation chamber of the CCE system, and lymphocytes were subsequently eluted with 700 ml of elutriation buffer at a flow rate of 11 ml/min and a rotor speed of 2080 rpm for a period of 60 min. The residual MO were removed from the elutriation chamber under sterile conditions, washed twice in PBS, then resuspended in supplemented RPMI containing no serum. The MO recovery was approximately $1\times10^8$ cells and viability as determined by trypan blue exclusion was 96%.

Human monokine-enriched supernatant preparations.

For preparation of enriched supernatants, cells populations were isolated as described above, suspended in serum-free RPMI medium ($2\times10^6$ cells/ml) containing all supplements noted previously, and stimulated with 10 µg/ml of *Escherichia coli* LPS (055: B5: Difco, Detroit, Mich.). Control supernatants were generated as indicated, but without the addition of LPS. The supernatant was collected after incubation at 37° C. in 5% $CO_2$ (for 24 h, unless otherwise indicated) and centrifuged for 10 min at 2000 rpm. Supernatants were aliquoted and stored at −20° C.

Induction of HIV-1 expression in ACH-2 cells.

ACH-2 cells were cultured in complete medium alone or in complete medium containing cell supernatant preparations (% v/v as indicated in text), IUdR (100 µg/ml), or PMA ($10^{-8}$M). When $0.5\times10^6$ cells were used, inductions were carried out in 24-well tissue culture plates (Costar) in a total volume of 1 ml. When $5\times10^6$ cells were used, cultures were maintained in a total volume of 10 ml in upright 25-cm$^2$ tissue culture flasks (Corning). All cultures were kept at 37° C. in 5% $CO_2$ for the time periods indicated in the text.

Determination of apparent m.w. by gel filtration.

A total of 200 ml of LPS-MO SN was concentrated to 20 ml in an Amicon stirred cell using a YM-2 membrane (M. cutoff of 1 kDa) at 4° C. A 2-ml aliquot of this material was loaded onto a 2.5×100 cm sephacryl S-200 column (Pharmacia Fine Chemicals, Uppsala, Sweden) in PBS, pH 7.2, at 4° C. Then 5-ml fractions were collected, and 2-ml aliquots from the even numbered fractions were filter sterilized (0.22 µm filter). These aliquots were then tested for biologic activity on ACH-2 cells, assayed for human IL-1β by RIA (Cistron Technology, Pinebrook, N.J.) or assayed for human TNF-α using an ELISA. The ELISA assay used affinity purified rabbit polyclonal antibody to human rTNF-α (Cetus Corp., Emeryville, Calif.). The reaction was developed with horseradish peroxidase-conjugated rabbit anti-rTNF-α. This assay has less than 2% cross reactivity with TNF-β.

Removal of monokine activity by pre-coupled immunoaffintiy gels.

Aliquots (1 ml) of unconcentrated LPS-MO SN were incubated with varying concentrations of agarose immunoaffinity gel for human TNF or pre-immune IgG control agarose (Endogen, Inc., Boston, Mass.) for 2 h at 37° C. After centrifugation for 2 min at 20,000×g, supernatants were removed and tested for biologic activity on ACH-2 cells.

RESULTS

Isolation and characterization of human T cell clone latently infected with HIV-1.

A3.01 cells (Folks et al, supra) were infected with HIV-1 at a multiplicity of infection equal to one infectious unit/cell. Four days after infection, cells were cloned at 0.2 cells/well in 0.2 ml of culture medium. Aliquots of 192 clones derived from 960 microcultures were pooled in eight groups containing 24 clones, treated with IUdR, which is a known inducer of retrovirus expression (Lowry et al, 1971, *Science*, 174:155), and then co-cultivated with fresh A3.01 cells. Inasmuch as the majority of A3.01 cells surviving infection with HIV-1 are CD4−(Folks et al, supra), they must be cocultivated with $CD4^+$ A3.01 cells to easily identify virus expressing cells. Virus induction and expression was monitored daily by screening the co-cultures for syncytia formation. One of the eight groups displayed syncytia and aliquots of the individual clones comprising this group were subjected to a second cycle of IUdR treatment followed by A3.01 co-cultivation. Six of the 24 clones within this group produced syncytia when co-cultured with A3.01 cells after exposure to IUdR. Of these, a single clone (ACH-2) was isolated that produced syncytia and detectable supernatant RT activity.

Surface characterization of ACH-2 by FCM revealed that the cloned cells stained positive for Leu 1 (CDS), MHC class I Ag, and transferrin receptors, but had no detectable expression of Leu 3(CD4), Leu 4 (CD3), Leu 2 (CDS), or MHC class II (HLA-DR) determinants. Restriction enzyme analysis of cellular DNA from this clone, using Southern blot hybridization to determine the number and state of HIV-1 proviral DNA copies, revealed the presence of a single integrated copy of proviral DNA (data not shown).
Activation of HIV expression.

In addition to IUdR, it was anticipated that PMA might be a suitable agent to use as an inducer to investigate the mechanisms of HIV activation. The ACH-2 clone was tested and found to exhibit increased levels of RT activity when cultured in the presence of $10^{-8}M$ PMA. This clone was then selected as a model to analyze the effect of cellular-derived products implicated in T cell activation, particularly monokines, on the activation of HIV-1 expression in chronically or latently infected T cells.

Using the tumor promoter PMA as an HIV-1 induction control, it was determined whether the ACH-2 clone could also respond to a monokine-enriched supernatant derived from bacterial endotoxin-stimulated human monocyte-macrophages (LPS-M0 SN) by expressing HIV-1. A crude monokine-enriched supernatant preparation was initially chosen to determine whether any induction could be detected, because such an effect may or may not ultimately be attributable to known monokines, and/or may require the interactions of multiple factors. As shown in FIG. 1, ACH-2 cells cultured with either PMA or LPS-M0 SN have significantly increased RT activity relative to the uninduced ACH-2 cells cultured in medium alone. Inasmuch as this could reflect an increase in virus release rather than an increase in virus production, vital proteins present in induced and uninduced ACH-2 cells were concomitantly analyzed by immunoblotting, using serum from an AIDS patient which contained antibodies to the standard HIV-1 proteins. Comparative analysis of expressed HIV-1 proteins in the ACH-2 line with a control lysate derived from HIV-1-infected A3.01 cells revealed low levels of detectable p55, p41, and p24 proteins in the uninduced ACH-2 cells (FIG. 1), which represent gag gene products. In contrast, ACH-2 cells stimulated with PMA or LPS-M0 SN had detectable levels of all major HIV-1 proteins, including three env gene products gp160, gp120, and gp41, p64 (RT), as well as the gag proteins p55, p24, and p18. It is not known whether this observed difference in protein patterns between induced and uninduced cells was qualitative in nature, because prolonged exposure of immunoblots of uninduced cells subsequently revealed low levels of some, but not all, of the other major HIV-1 proteins (data now shown).

Figure 2C:
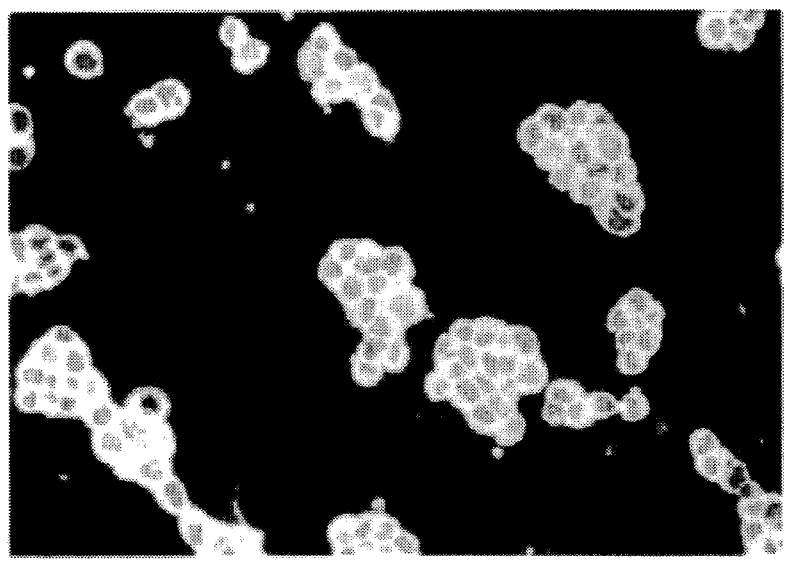
FIG. 2A–2C show immunofluorescent analysis of HIV-1 protein expression in ACH-2 cells ($5 \times 10^6$) that were cultured as indicated in FIG. 1 in complete medium. Aliquots of cells were cytospun, air dried, and fixed in acetone/methanol. The percentage of cells expressing intracellular viral proteins was determined by indirect immunofluorescence using serum from a single AIDS patient and FITC-conjugated goat anti-human Ig antibody. Slides were observed for fluorescence-positive cells on a Nikon Labfot fluorescence microscope.
Figure 2B:
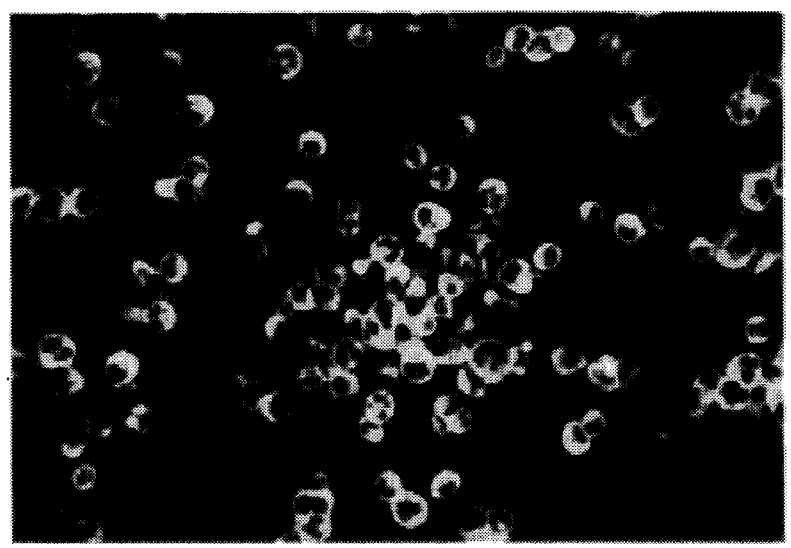
Figure 2A:
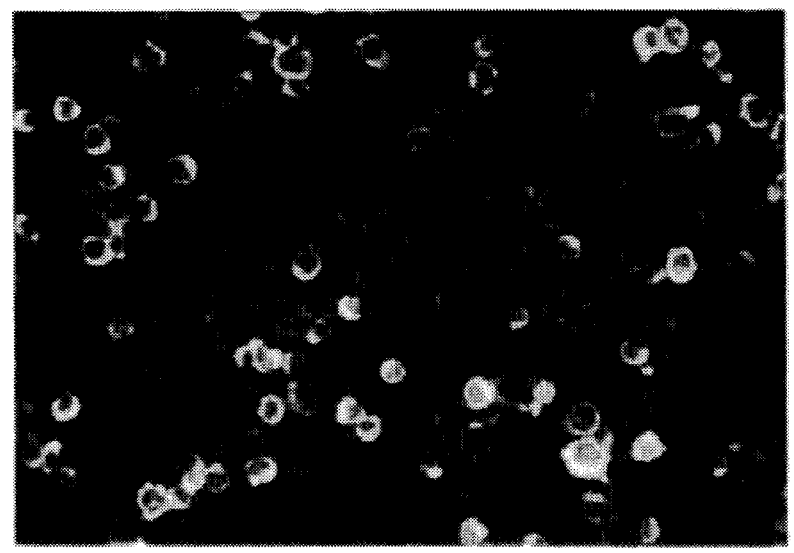

Increased expression of HIV-1 proteins demonstrable after induction of ACH-2 cells could result either from an increase in virus production from cells exhibiting low levels of virus expression or from the induction of virus from cells in a nonproductive latent state. To determine to which category the ACH-2 cells belonged, induced and uninduced cells were analyzed by indirect immunofluorescence using an AIDS patient's serum and FITC-conjugated goat anti-human Ig. Examination of the uninduced ACH-2 cells revealed that only 10 to 15% of the cells constitutively expressed detectable amounts of proteins reactive with the anti-HIV-1 antiserum, whereas 100% of the cells showed positive immunofluorescence after induction (FIG. 2). Because of this, subclones were derived from ACH-2 by limiting dilution to confirm its clonality and reaffirm its inductbility.

Of 29 subclones obtained from two separate clonings, 27 exhibited patterns of inducible RT activity that were similar to parental ACH-2 cells, whereas two subclones were non-inducible. In situ hybridization using an HIV-1 ribo probe on the parental ACH-2 cells revealed that only 2% of the cells were strongly positive for HIV-1 mRNA, whereas 20% of the cells had levels that were slightly above background. The majority of cells had no detectable HIV-1 mRNA. Subsequent in situ hybridization analysis of 12 of the subclones derived from ACH-2 cells revealed similar percentages of reactivity. This suggested that the ACH-2 cells were a homogeneous clone of cells infected with HIV-1, but varying with regard to virus expression, with most cells existing in a non-productive state.

The infectious nature of the particles produced after induction was of critical importance because no HIV-1-infected cellular clone producing infectious virus has been reported. This was examined by titrating cell-free filtered supernatants, derived from ACH-2 cells cultured for 48 h in medium or in medium containing LPS-M0 SN, onto human PBMC that were stimulated with PHA. Observation of the cultures for cytopathic effect and analysis of the culture supernatant for RT activity for 12 days revealed that infectious virions were detectable in the uninduced cultures at a final dilution of $10^{-1}$. However, the production of infectious virus was found to be increased by 100-fold ($10^3$ infectious units) after induction with LPS-M0 SN.
Determination of optimal conditions for induction of ACH-2 cells.

Figure 3A:
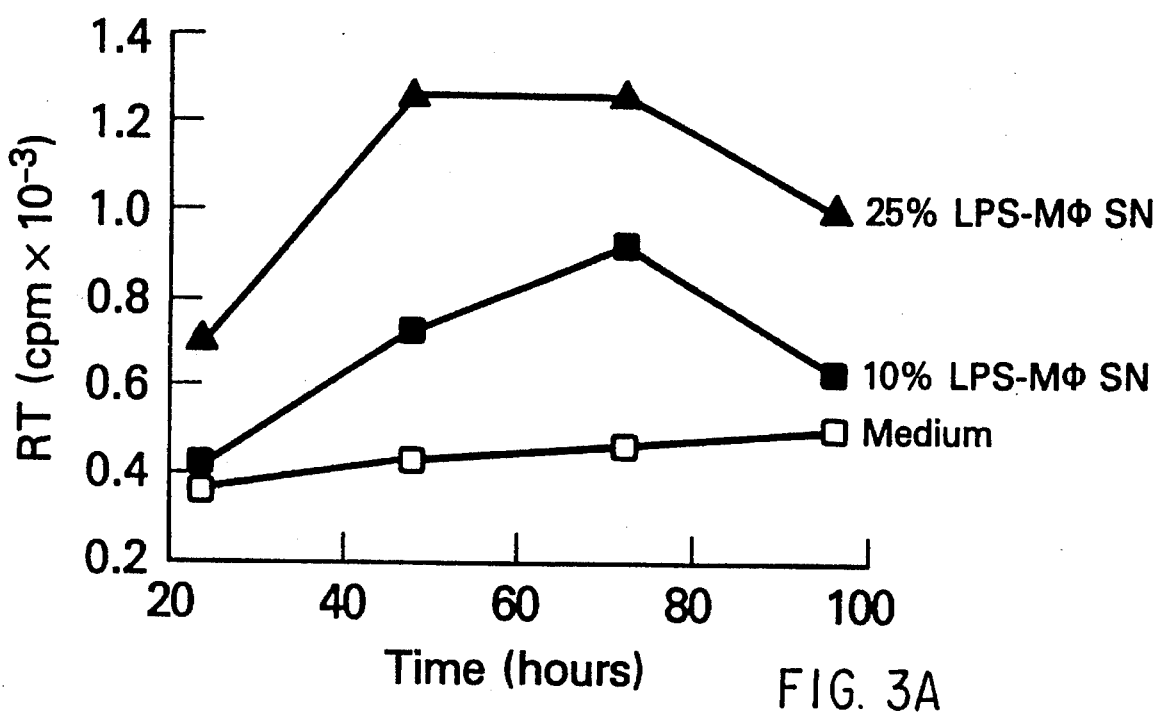
FIGS. 3A–3B show kinetics of induction of ACH-2 cells and dose response to LPS-M0 SN. ACH-2 cells ($0.5 \times 10^6$) were cultured in complete medium in the presence or absence of varying concentrations of LPS-M0 SN. Two concentrations of LPS-M0 SN (20% and 25%) were selected. Aliquots of culture supernatants were removed at various time points, stored at $-70°$ C., then assayed for RT activity using the $^3$H-TTP assay to determine the kinetics of induction. Data are expressed as counts/min/8 μl of supernatant.
Figure 3B:
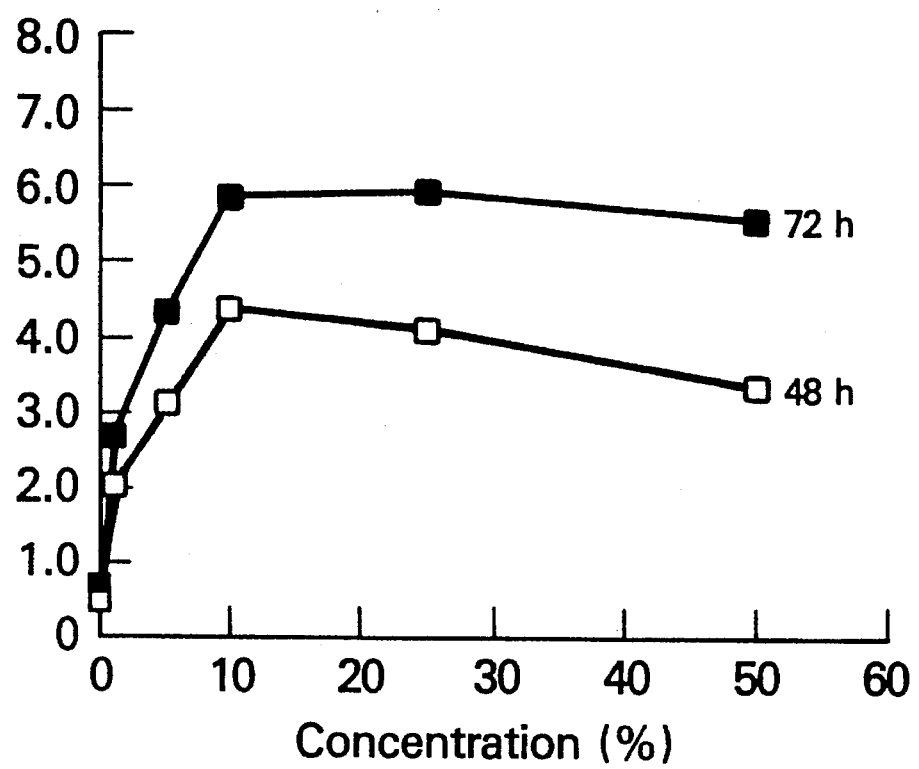

Inasmuch as the conditions used for the initial induction of ACH-2 cells were based on those previously established for the cytokine induction of a chronically HIV-1-infected promonocyte clone (Folks et al, 1987, *Science*, 238:800), efforts were made to ascertain the optimal conditions for the induction of the latently infected T cell clone. As shown in FIG. 3A, optimal induction occurred 48 or 72 h after culture of ACH-2 cells with LPS-M0 SN, depending on the concentration of supernatant. Furthermore, the level of induction was also dependent on the concentration of the cytokine, with a final supernatant concentration of 10 to 25% being optimal for inducing virus expression (FIG. 3B). Analysis of RT activity after the culture of ACH-2 cells in medium containing 10 µg/ml of LPS or M0 SN lacking LPS demonstrated that LPS alone was not capable of inducing virus production, whereas Me SN alone could slightly augment HIV-1 expression (data not shown). This increased virus production could not be attributed to release of virus secondary to a toxic effect, because the ACH-2 cells remained 65 to 70% viable after 5 days of culture with LPS-M0 SN at the optimal inducing concentrations. This suggested that the human monocytes exposed to LPS were producing a factor(s) that was capable of interacting with the ACH-2 cell clone to induce expression of HIV.

Kinetics of cytokine production.

Figure 4:
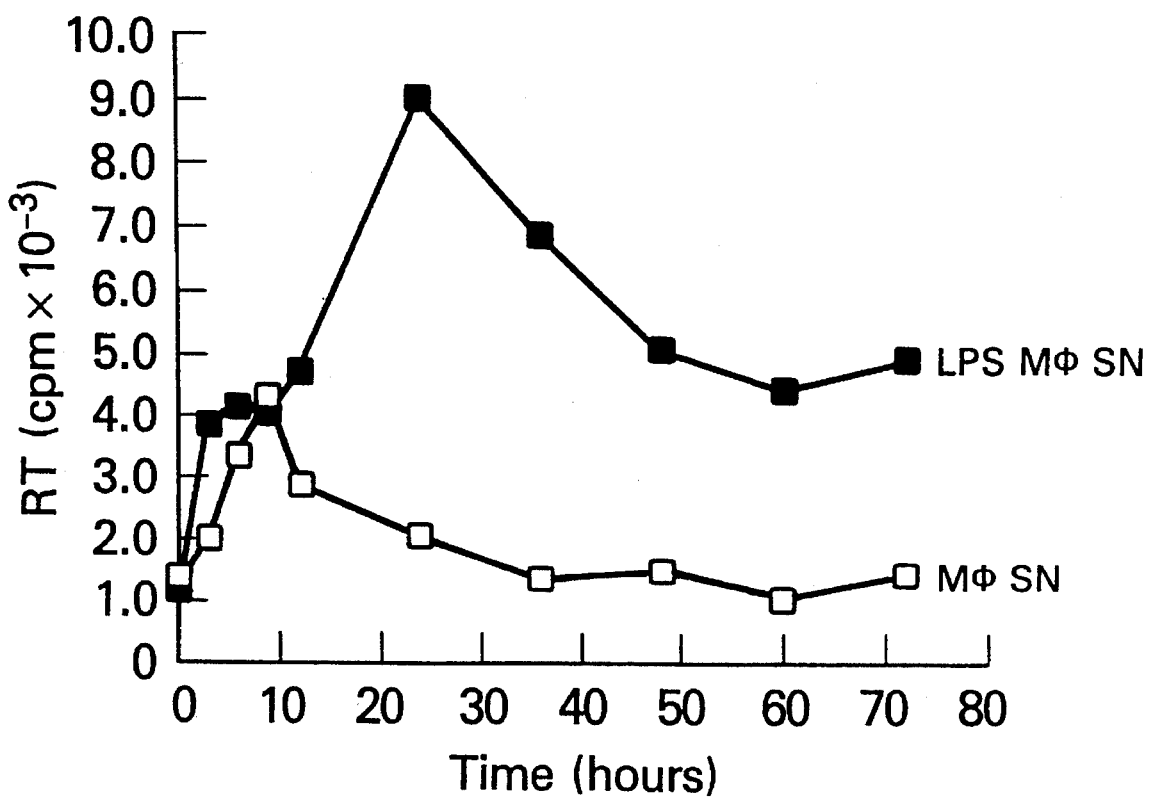
FIG. 4 shows kinetics of the production of M0 factor(s) capable of inducing ACH-2 cells. Normal human PBMC were obtained after leukopheresis and cell separation on a Ficoll-Hypaque density gradient. M0 were isolated by countercurrent centrifugal elutriation (Beckman rotor JE-6), and were cultured ($2 \times 10^6$ cells/ml) in RPMI in the presence and absence of *Escherichia coli* LPS (055: B5: 10 μg/ml). Aliquots removed from the cultures at various time points were centrifuged, the supernatant was removed, and stored at $-20°$ C. M0 SN and LPS-Mπ SN (10% v/v) were then cultured with ACH-2 cells ($0.5 \times 10^6$) for 48 h and culture supernatants were removed and assayed for RT activity (cpm/8 μl) using $^3$H-dTTP.

To determine the kinetics of the production of this factor(s), elutriated human monocytes were cultured in serum-free medium in the presence or absence of bacterial LPS. As shown in FIG. 4, monocytes release some substance(s) capable of inducing ACH-2 cells (as indicated by increased RT activity) within 9 h after culture in medium, independent of the presence of LPS. However, the greatest induction of HIV-1 production occurred when a supernatant obtained 24 h after culturing human monocytes with LPS was used (FIG. 4). It was also observed that this factor(s) was either not stable upon prolonged culture, or that other factors also produced by the macrophages were capable of inactivating or inhibiting the inducing substance as evidenced by the loss of inductbility with time (FIG. 4).

Characterization of cell type producing HIV-inducing cytokine.

The fact that the cell population stimulated with bacterial LPS was obtained by countercurrent centrifugal cell elutriation and should be predominantly M0, and the fact that LPS is known to elicit cytokine production from human monocytes to a greater extent than from B and T lymphocytes, strongly suggested that the substance(s) involved in the induction of HIV-1 expression was produced by cells of the monocytic lineage. However, it is also known that many cytokines are produced by multiple cell types (Dinarello, C. A., 1984, *Interleukin*-1. *Rev. Infect. Dis.*, 6:51; Tracey et al, 1988, *J. Infect. Dis.*, 157:413; Clark et al, 1987, *Science*, 236:1230). Therefore, it was necessary to confirm that the cell population producing this factor(s) was in fact the monocyte. This would facilitate selection of recombinant cytokines for subsequent testing and/or assist in determining appropriate conditions for biochemical characterization of the factor(s).

Human mononuclear cells were obtained by leukopheresis of peripheral blood using parameters that would preferentially enrich for monocytes rather than T lymphocytes. The PBMC obtained following Ficoll-Hypaque isolation were then subjected to various treatments to obtain purified or enriched populations of monocytes and T lymphocytes. Monocytes were obtained by elutriation, as noted above, and T lymphocytes were obtained by a method described previously (Clouse et al, supra) using a reagent containing a cocktail of mAb and C. When analyzed for cell surface immunofluorescence, it was shown that the elutriated cells contained minimal (3%) Leu 4$^+$T cells with 82% staining positive for Leu M3 when compared to untreated control PBMC, indicating that the population was significantly enriched for monocytes. In contrast, the cells treated with the T lymphocyte isolation reagent contained no detectable Leu M3$^+$ cells with 90% staining positive for Leu4, indicating that this population of cells was predominantly T lymphocytes. The enriched cell populations and control PBMC were then used to determine the cell type responsible for production of the factor(s) capable of inducing HIV expression in this T cell clone.

Figure 5:
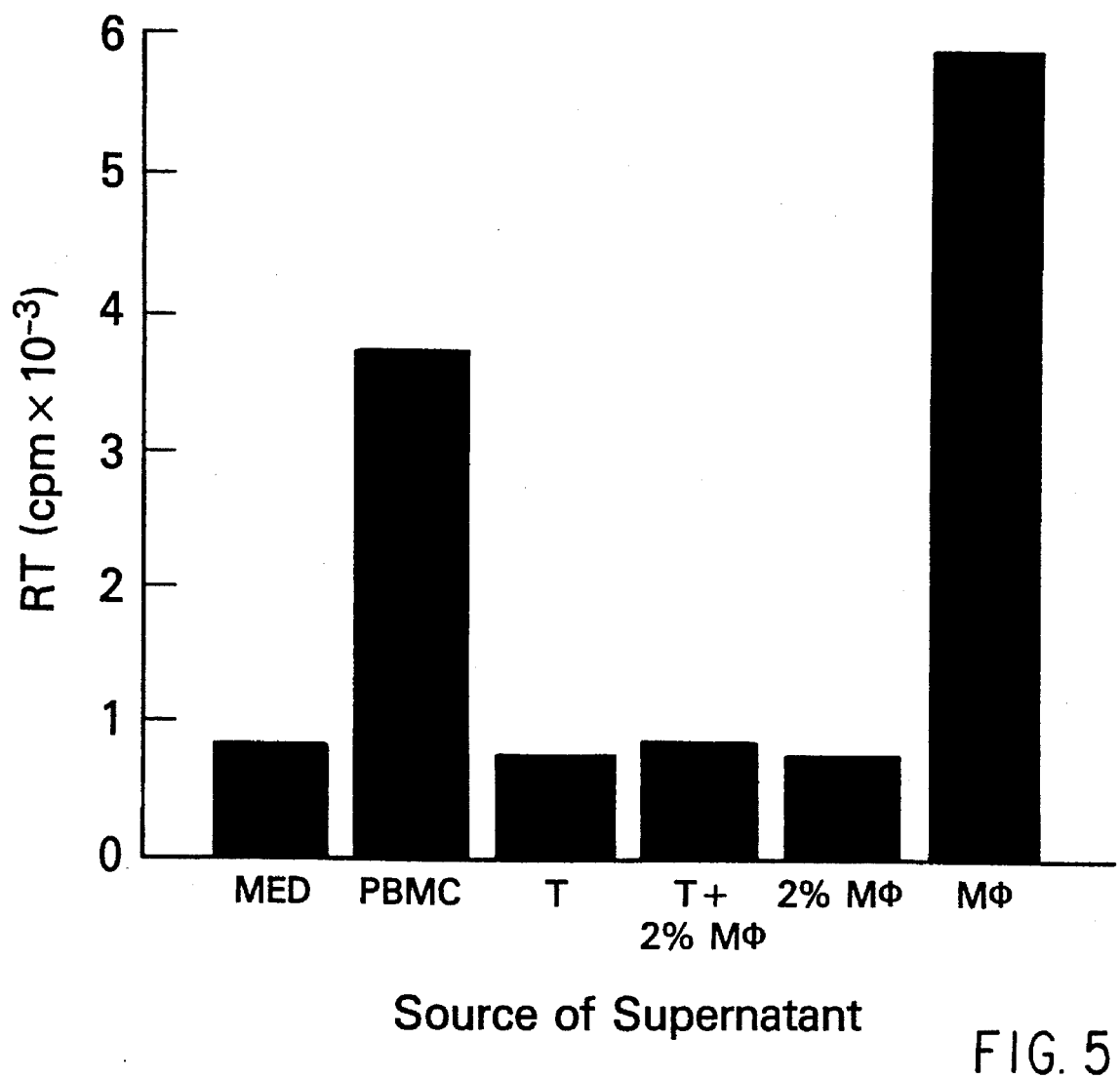
FIG. 5 shows induction of ACH-2 cells with supernatants from various LPS-stimulated mononuclear cell populations. PBMC, enriched T lymphocytes and elutriated M0 isolated as indicated in the text were cultured in RPMI ($2\times10^6$ cells/ml) for 24 h in the presence of LPS (10 μg/ml). T cells with $4\times10^4$ M0/ml (labeled as T+2% Mf) or an equivalent number of M0 alone (labeled as 2% M0) were cultured in parallel. Supernatants derived from these cultures were tested (10% v/v) for their ability to induce HIV-1 expression as measured by increased RT activity (counts/min/8 μl) from ACH-2 ($0.5\times10^6$) cells after 48 h of incubation.

Control PBMC, enriched T lymphocytes, and elutriated monocytes were cultured for 24 h in medium in the presence or absence of LPS (10 µg/ml). To exclude the possibility that T cells were responsible for production of the inducing factor but required the presence of a minimal number of accessory cells, parallel cultures containing enriched T cells supplemented with a 2% final concentration of monocytes or an equivalent number of monocytes cultured in the absence of T lymphocytes were also prepared. These 224-h supernatant preparations were then tested for their ability to induce HIV-1 expression in ACH-2 cells. It was found that all supernatants derived from cells cultured in the absence of LPS had inductive capacities that were less than their LPS-stimulated cell counterparts. Unfractionated PBMC stimulated with LPS could produce a factor(s) capable of inducing virus expression, as measured by an increase in RT activity (FIG. 5). In contrast, supernatants from enriched T cells cultured alone or with minimal numbers of accessory cells in the presence of LPS failed to augment HIV-1 expression in ACH-2 cells. However, the highest level of RT activity occurred when the cloned ACH-2 cells were cultured in the presence of supernatant obtained after the 24-h culture of elutriated monocytes with LPS (FIG. 5), suggesting that the inducer(s) involved was in fact a product secreted from M0.

Biochemical characterization of inductive component present in LPS-M0 SN.

Figures 6A, 6B:
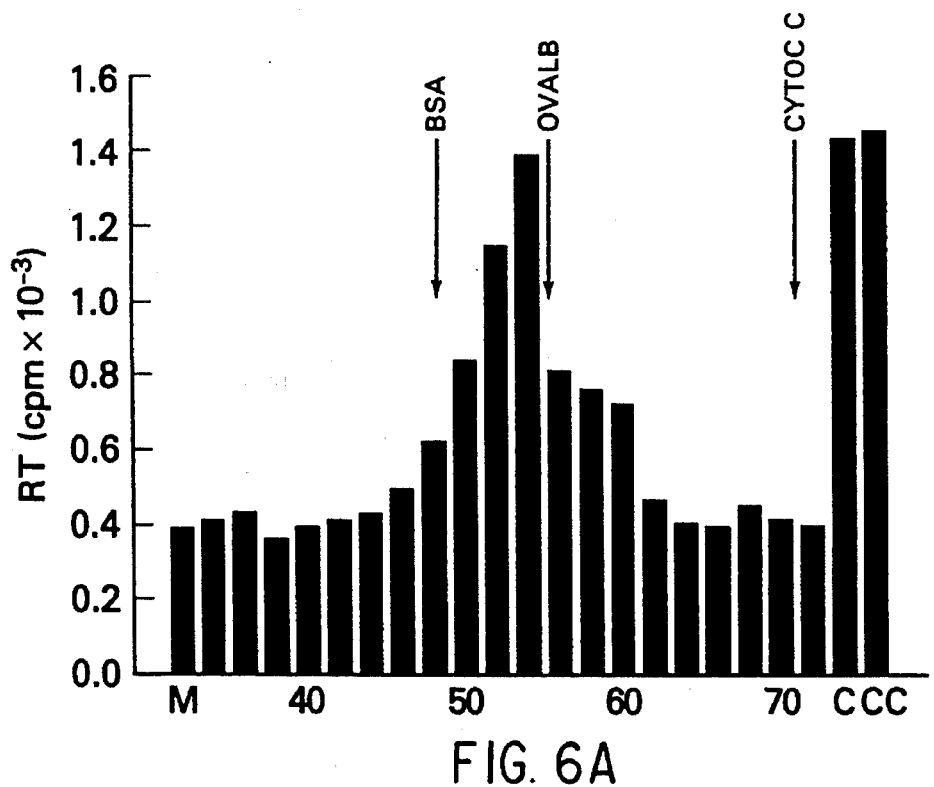
FIGS. 6A–6B show biologic induction of Sephacryl S-200 fractionated LPS-M0 SN. LPS-M0 SN (200 ml) was concentrated 10-fold at 4° C. using an Amicon filtration unit with a YM-2 membrane (Mr cutoff=1 kDa). An aliquot (2 ml) of concentrated material was loaded onto a 2.5×10 cm Sephacryl S-200 column in PBS, pH 7.2 also at 4° C. Fractions were collected, filter sterilized (0.22 μm), and alternate fractions were then tested for biologic activity on ACH-2 cells as reflected by RT activity (A). ACH-2 control cultures included medium along (M), unconcentrated LPS-M0 SN (C) and 10×concentrated LPS-M0 SN (CC). All fractions and control C were tested at 10% (v/v), whereas control CC was tested at 1%. The elution profile of Mr standards BSA (68 kDa). OVALB (43 kDa), and cytochrome C (12 kDa) are also indicated.

Biochemical analysis of the LPS-M0 SN preparation was initiated to determine whether one or multiple factors were involved in the induction of HIV-1 expression by ACH-2 cells. The LPS-M0 SN was concentrated 10-fold and then fractionated on a Sephacryl S-200 sizing column, and the individual fractions were tested for their ability to induce virus expression. As shown in FIG. 6A, the inductive activity as assessed by RT activity chromatographed as a broad but single peak, consistent with one factor responsible for the activity. Furthermore, based on the profile generated, the inducing factor appeared to have a $M_1$ of approximately 45 kDa (FIG. 6A).

The S-200 fractions from concentrated LPS-M0 SN were also tested for the presence of monokines that have been well characterized and that may participate in this induction response. LPS-stimulated human M0 are known to produce TNF-$\alpha$ and IL-1 which are proteins having multiple biologic activities that are released in vivo in response to invasive stimuli. As shown in FIG. 6B, when the S-200 fractions were analyzed by RIA for IL-1 activity, quantities exceeding 400 µg/ml were detected in fractions 58 through 70, whereas no detectable IL-1 was present in those fractions (50 through 56) capable of inducing HIV-expression in ACH-2 cells. In contrast, those fractions (50 through 56) having levels of human TNF-$\alpha$ detectable by ELISA (100 to 300 µg/ml) were the same fractions responsible for the induction of virus production (FIG. 6A and B), suggesting that TNF-$\alpha$ may be the active component present in the LPS-M$\pi$ SN.

Figure 7:
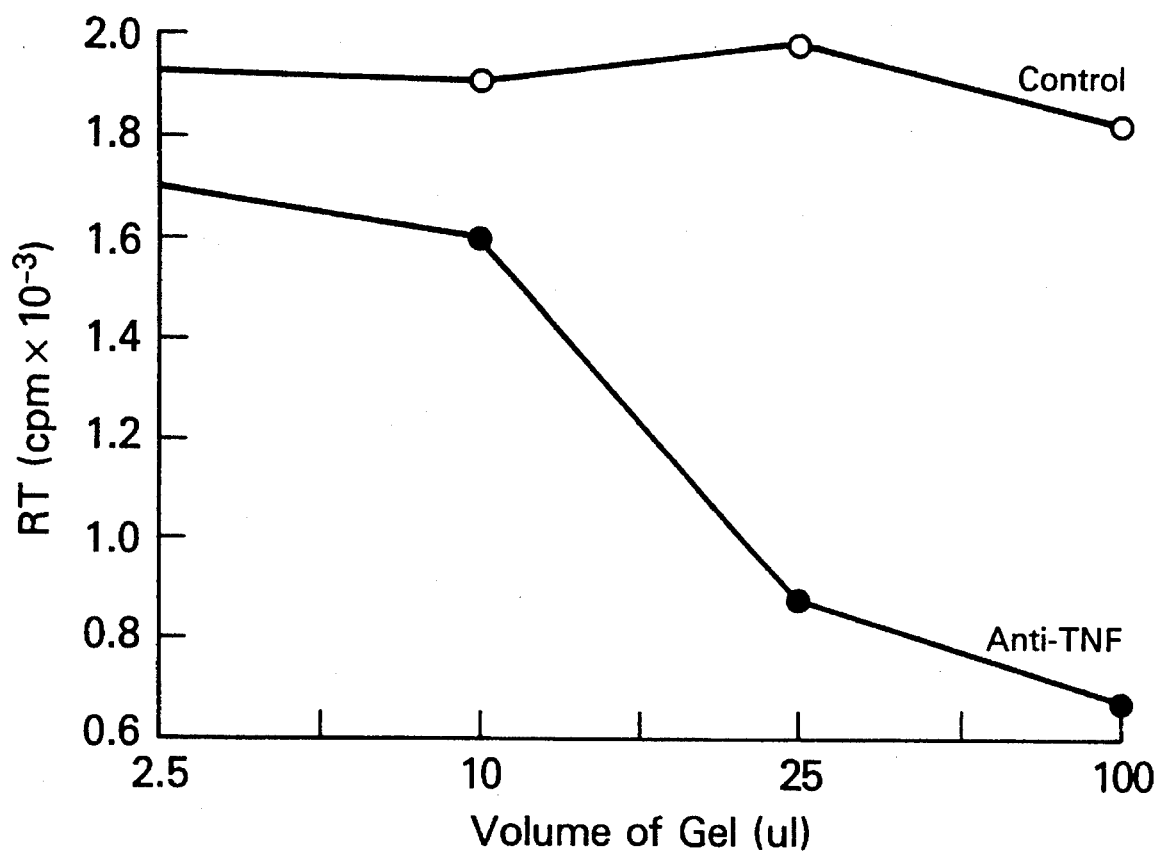
FIG. 7 shows immunoabsorption of the biologically active component from LPS-M0 SN. Aliquots (1 ml) of unconcentrated LPS-M0 SN were incubated with varying volumes (μl) of human TNF-α immunoaffinity gel (anti-TNF-α) or agarose coupled to pre-immune rabbit IgG antibodies (control) for 2 h at 37° C. with end-over-end mixing. Absorbed supernatants were collected following centrifugation at 10,000×g and were tested for biologic activity on ACH-2 cells at 25% (v/v) final concentration. Induction of HIV-1 expression was measured by increased RT activity from ACH-2 cells ($0.5\times10^6$) after 48 h of incubation. Culture of ACH-2 cell incubated in medium alone had levels of RT activity resulting in 0.65 counts/min×$10^{-3}$.

Aliquots of unconcentrated LPS-M0 SN were subsequently absorbed with increasing volumes of agarose gel pre-coupled to either rabbit antibody to human TNF-$\alpha$ (anti-TNF) or pre-immune rabbit IgG (control). As shown in FIG. 7, supernatants absorbed with the contnrol gel varied little in their ability to induce HIV expression in ACH-2 cells, as assessed by RT activity. In contrast, LPS-M0 SN absorbed with the immunoaffinity gel for TNF-α displayed a dose-dependent removal of their inductive capacity on the HIV-infected cells.

In summary, a human T cell clone has been isolated from cells surviving acute infection with HIV-1 whose expression of virus is enhanced after treatment with supernatants derived from LPS-stimulated normal human peripheral blood monocytes. The chronically infected T cell clone (ACH-2) produces little virus in an uninduced state, but has markedly increased production of infectious virus upon stimulation with PMA. This provides a model of a cloned, HIV-infected T cell line with which to examine a range of stimuli capable of converting a minimally HIV-expressing cell to a highly productive one.

Availability of the chronically infected cell line of the present invention also provides a control for quantitation in PCR assays (Schnittman et al, 1989, *Science*, 245:305–308).

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A human T-cell clone obtained from A3.01 cells containing an integrated copy of human immunodeficiency virus in a latent state, where said clone is a means by which to test whether a substance can induce said virus to productive multiplication in an in vitro system, wherein said substance does not induce said virus to productive multiplication by stimulating CD3 complex on said human T-cell clone and wherein said substance is extracted from bacterial endotoxin-stimulated human peripheral blood monocytes.

* * * * *